United States Patent [19]

Eisenberg

[11] Patent Number: 4,787,376
[45] Date of Patent: Nov. 29, 1988

[54] RETAINER FOR GLOVE

[75] Inventor: Joel H. Eisenberg, 410 Morehouse Rd., Easton, Conn. 06612

[73] Assignee: Joel H. Eisenberg, Easton, Conn.

[21] Appl. No.: 21,172

[22] Filed: Mar. 3, 1987

[51] Int. Cl.⁴ .............................................. A61F 5/10
[52] U.S. Cl. .......................................... 128/77; 2/21; 2/161 R; 2/161 A; 128/880
[58] Field of Search ............... 128/88, 77, 89 R, 153, 128/85, 165, 133, 87 R, 87 A; 2/16, 22, 17, 18, 19, 20, 21, 161 R, 161 A

[56] References Cited

U.S. PATENT DOCUMENTS

| 381,687 | 4/1888 | Fischer | 2/19 |
|---|---|---|---|
| 1,471,948 | 10/1923 | Cox et al. | 128/89 R |
| 1,509,801 | 9/1924 | Walters | 2/19 |
| 1,627,382 | 5/1927 | Golomb | 2/18 |
| 1,817,212 | 8/1931 | Siebrandt | 128/85 |
| 1,837,691 | 12/1931 | Thigpen | 128/87 A |
| 1,951,190 | 3/1934 | Gambee | 2/21 |
| 2,388,330 | 11/1945 | Jungmann | 2/16 |
| 2,498,122 | 2/1950 | Haniuk | 128/133 UX |
| 2,523,606 | 9/1950 | Young | 128/87 A |
| 2,633,126 | 3/1953 | Newmark | 128/133 |
| 3,182,657 | 5/1965 | Zurbuchen | 128/133 |
| 3,416,158 | 12/1968 | Kulman | 2/161 R |
| 3,605,117 | 9/1971 | Latina | 2/16 |
| 3,724,456 | 4/1973 | Waxman | 128/133 |
| 3,882,548 | 5/1975 | Shinagawa et al. | 2/161 A |
| 4,137,572 | 2/1979 | Jansson et al. | 2/16 |
| 4,173,218 | 11/1979 | Cronin | 128/77 |
| 4,243,026 | 1/1981 | Barber | 128/77 |
| 4,287,610 | 9/1981 | Rhee | 2/18 |
| 4,295,229 | 10/1981 | Clark et al. | 2/20 |
| 4,438,532 | 3/1984 | Campanella et al. | 2/16 |
| 4,445,507 | 5/1984 | Eisenberg | 128/87 A X |
| 4,524,464 | 6/1985 | Primiano et al. | 2/17 X |
| 4,565,195 | 1/1986 | Eisenberg | 128/165 X |
| 4,653,490 | 3/1987 | Eisenberg | 128/133 |
| 4,658,441 | 4/1987 | Smith | 2/21 X |

Primary Examiner—Edgar S. Burr
Assistant Examiner—Moshe I. Cohen

[57] ABSTRACT

A removable retainer for the radical side of the thumb pocket of a glove, which retainer restricts the radial movement of the thumb in the glove away from the other fingers so as to prevent damage to the ligaments of the thumb should radial force be applied to the thumb.

3 Claims, 1 Drawing Sheet

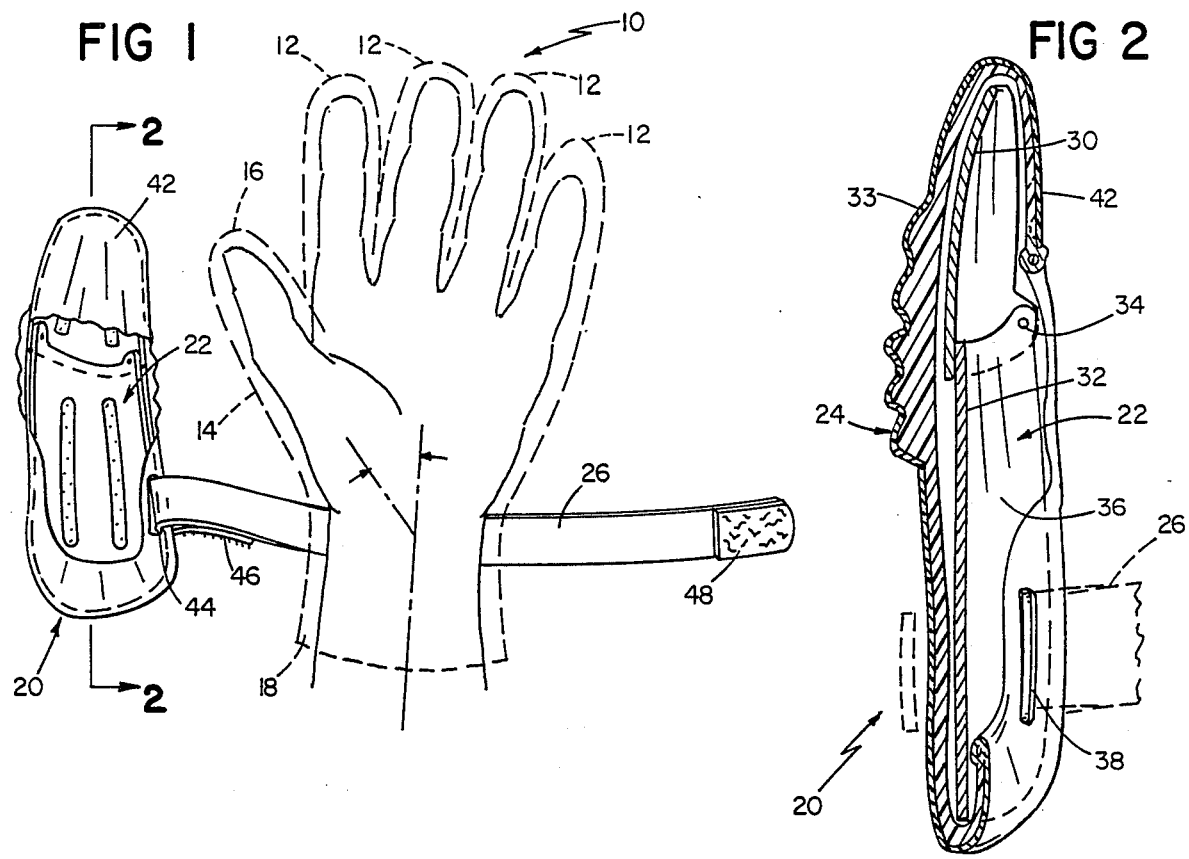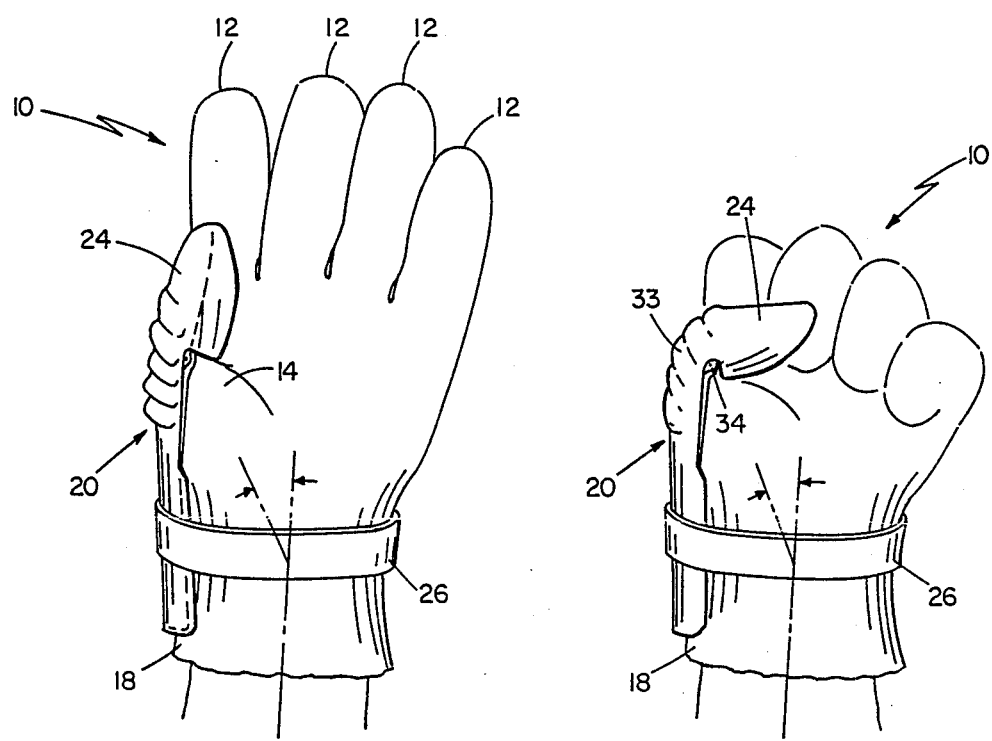

RETAINER FOR GLOVE

FIELD OF THE INVENTION

This invention relates to the field of protective handwear, particularly in regard to preventing damage to certain ligaments of the thumb.

BACKGROUND OF THE INVENTION

In various sports and recreational activities, as well as in industry, there are numerous occasions when, as a result of a fall or other event, the thumb is momentarily bent away from the other fingers of the hand. This bending results in a stretching of the ulnar collateral ligament which is connected around the thumb's lower joint, the metacarpal phalageal joint. If this stretching is severe enough, the ligament will rupture, and as it will frequently not heal by itself, surgery is often required to repair the tear. Even if the ligament is not torn, such a stretching, particularly if repeated, will loosen the ligament giving rise to a chronic wobbling of the joint, which could cause arthritis.

Most prior art gloves and handwear are, at best, only designed to protect the hand from cold or from abrasions and do not prevent such ligament damage at all. Furthermore, the common way to protect the thumb area after surgery is by using a cumbersome cast, which cannot, as a practical matter, be kept on the hand for longer than six to eight weeks, a time period far short of that actually required for the ligament to mature. Accordingly, there is a need for more adequate protection for the thumb ligaments, and in particular, a need for a protective means which can be used with existing gloves.

SUMMARY OF THE INVENTION

I have discovered that stress on the ulnar collateral ligament can be greatly reduced while allowing the thumb and hand generally normal freedom of movement by effectively restraining the thumb from radial movement by means of a retainer which attaches to the radial side of the thumb portion of a glove.

In a preferred embodiment, stress on the ulnar collateral ligament can be greatly reduced by attaching a retainer having an upper and lower piece connected by a hinge to the outside of the thumb portion of a glove so that, when the glove is on the hand with the retainer in place, radial movement of the thumb is limited while the upper joint of the thumb can bend normally in the ulnar direction. When the user's thumb is in place in said thumb portion of the glove and the retainer is in place, the retainer is extended over the radial side of the thumb's metacarpal phalageal joint and is of sufficient length to also extend over substantial portions of the adjacent bones which form the joint so as to generally immobilize the bones with respect to the joint in the radial direction whereby radial movement of the thumb which might injure the ulnar collateral ligament is prevented.

DESCRIPTION OF THE PREFERRED EMBODIMENTS

I turn now to the description of the preferred embodiment after first briefly describing the drawings.

FIG. 1 is a first view of a retainer of the preferred embodiment;

FIG. 2 is a sectional view of a retainer of FIG. 1;

FIG. 3 is a second view of a glove with the retainer in place; and

FIG. 4 is view of the glove with the retainer in a flexed position on a glove.

STRUCTURE

The preferred embodiment of the invention is shown in FIG. 1. The glove 10 has four finger portions 12 and a thumb portion 14. A retainer 20, best shown in FIG. 2, fits over the thumb portion 14 and extends from the tip 16 of the thumb portion 14 to the wrist area 18. The retainer 20 covers the thumb's metacarpal phalageal joint and is of sufficient length to also extend over substantial portions of adjacent bones which form the joint. The retainer 20, itself, is comprised of a trough 22, a cover 24, and a strap 26.

The trough 22 has an upper piece 30 and a lower piece 32 connected by a hinge 34. The trough 22 is curved, having a hollow section 36 extending its entire length. The hollow section 36 conforms to the radial side of the thumb and hand of the glove 10 down to its wrist area 18. The lower piece 32 has a slit 38 near an edge 40 on the side disposed towards the finger portions 12 of the glove 10 when the retainer 20 is in place. The trough 22 may be made of fiberglass or any other material which can be easily molded but is lightweight and inflexible when hardened.

The cover 24 overlays the radial side of the trough 22 and encircles the ulnar side of the upper piece 30 to form a pocket 42 large enough to accommodate the tip 16 of the thumb portion 14 of the glove 10. The cover 24 also overlays the radial side of the lower piece 32. The cover 24 has a slit 44 corresponding to the slit 38 in the lower piece 32 of the trough 22. The section 33 of the cover that overlays the hinge 34 of the trough is flexible. The strap 26 is attached to the slits 38, 44 in the trough 22 and cover 24. The strap 26 is of sufficient length to extend around the lower part of the glove 10 when the retainer 20 is in place. A section 46 of the strap 26 adjacent to the slits 38, 44 as well as the end 48 of the strap 26 have fabric fasteners.

The retainer 20 fits over the thumb portion 14 of the glove 10 as shown in FIGS. 3 and 4. The lower portion of the retainer 20 is fastened securely to the glove 10 by wrapping the strap 26 tightly around the glove 10 and securing it with the fasteners. When the retainer 20 is in place, the hinge 34 is located adjacent to the upper joint of the thumb. The hinge 34 and flexible portion 33 of the cover 24 that overlays it allows the thumb to bend in the ulnar direction. The opposite radial movement of the thumb (which causes the injury to the ligament) is prevented as the secured trough 22 has essentially "frozen" the bones forming the lower thumb joint in the radial direction. As a result, the ulnar collateral ligament cannot be significantly stretched and thus is protected from damage.

What I claim is:

1. In combination, a glove having a thumb pocket and a removable retainer for selective use with the thumb pocket of said glove to prevent injury to the ulnar collateral ligament of the thumb of the glove's user, said retainer comprising:

a trough, said trough comprising a first part and a second part, said parts being connected together by a hinge which allows said first part to move only in an ulnar direction with respect to said second section when said retainer is in place said trough extending from the tip of the thumb portion of the glove to the wrist area and being generally inflexible in the radial direction when said retainer is in place on the thumb portion of the glove, said trough having a hollow section extending substantially its entire length, is hollow section adapted to fit partially around the radial side of the thumb pocket of the glove when said retainer is in place, a covering, said covering being disposed around said trough opposite said hollow section, a pocket, said pocket being connected to said covering at an end of said trough and extending over the adjacent portion of said hollow section leaving a space therebetween, said pocket being adapted to receive the tip of the thumb pocket of the glove when said retainer is in place, and a means for securing and unsecuring said retainer to the glove, said means for securing consisting of means designed and intended to be repeatedly removed and replaced at will and with minimal effort whereby when said means for securing is released, said retainer can be separated from the glove.

2. The retainer of claim 1 wherein said covering has a flexible portion disposed opposite said hinge.

3. The retainer of claim 1 wherein said means for securing comprises a strap connected to said trough, said strap adapted to fit around the wrist area of the glove.

* * * * *